United States Patent
O'Connor et al.

(10) Patent No.: US 10,485,513 B2
(45) Date of Patent: Nov. 26, 2019

(54) ULTRASOUND IMAGING APPARATUS

(75) Inventors: John P. O'Connor, Andover, MA (US); James W. Green, Lexington, MA (US)

(73) Assignee: Analogic Corporation, Peabody, MA (US)

( * ) Notice: Subject to any disclaimer, the term of this patent is extended or adjusted under 35 U.S.C. 154(b) by 690 days.

(21) Appl. No.: 13/017,344

(22) Filed: Jan. 31, 2011

(65) Prior Publication Data
US 2012/0197132 A1    Aug. 2, 2012

(51) Int. Cl.
| | | |
|---|---|---|
| *A61B 8/00* | (2006.01) | |
| *A61B 8/08* | (2006.01) | |
| *A61M 5/20* | (2006.01) | |
| *A61M 5/32* | (2006.01) | |
| *A61M 5/42* | (2006.01) | |

(52) U.S. Cl.
CPC ............ *A61B 8/469* (2013.01); *A61B 8/0891* (2013.01); *A61B 8/4427* (2013.01); *A61B 8/4455* (2013.01); *A61B 8/486* (2013.01); *A61M 5/20* (2013.01); *A61M 5/3287* (2013.01); *A61M 5/427* (2013.01); *A61M 2005/206* (2013.01); *A61M 2205/502* (2013.01)

(58) Field of Classification Search
CPC .................................................. A61B 8/4411
USPC ....................................................... 600/461
See application file for complete search history.

(56) References Cited

U.S. PATENT DOCUMENTS

| | | | |
|---|---|---|---|
| 4,058,114 A * | 11/1977 | Soldner ......................... | 600/461 |
| 4,363,326 A | 12/1982 | Kopel | |
| 5,398,690 A * | 3/1995 | Batten et al. ................ | 600/461 |
| 5,647,373 A | 7/1997 | Paltieli | |
| 5,769,086 A * | 6/1998 | Ritchart et al. .............. | 600/566 |
| 5,833,627 A | 11/1998 | Shmulewitz et al. | |
| 6,139,496 A * | 10/2000 | Chen ........................ | A61B 8/00 |
| | | | 600/437 |
| 6,336,899 B1 | 1/2002 | Yamazaki | |
| 6,527,731 B2 * | 3/2003 | Weiss et al. ................. | 600/566 |
| 6,569,102 B2 | 5/2003 | Imran et al. | |
| 6,599,272 B1 * | 7/2003 | Hjertman et al. ........... | 604/209 |
| 6,786,870 B2 | 9/2004 | Miyaki et al. | |
| 7,244,234 B2 * | 7/2007 | Ridley et al. ................ | 600/459 |

(Continued)

FOREIGN PATENT DOCUMENTS

| | | | |
|---|---|---|---|
| CN | 101310780 A | | 11/2008 |
| JP | 6105847 A | | 4/1994 |
| WO | WO2007130526 A1 | * | 11/2007 |

OTHER PUBLICATIONS https://dictionary.cambridge.org/us/dictionary/english/syringe.*

(Continued)

*Primary Examiner* — Rajeev P Siripurapu
(74) *Attorney, Agent, or Firm* — Anthony M. Del Zoppo, III; Daugherty & Del Zoppo Co. LPA

(57) ABSTRACT

An apparatus includes an ultrasound portion configured to acquire an image of a region of interest of a subject. The apparatus further includes an instrument carrying portion configured to carry and employ an instrument to perform a procedure at the region of interest based on the image. The ultrasound and instrument carrying portions are enclosed in the same enclosure. The apparatus, including both the ultrasound portion and instrument carrying portion, is configured to be transported and operated via at least a single hand of a user of the apparatus.

23 Claims, 10 Drawing Sheets

(56) References Cited

U.S. PATENT DOCUMENTS

| | | | |
|---|---|---|---|
| 7,653,427 | B2 | 1/2010 | Essner et al. |
| 7,699,776 | B2 | 4/2010 | Walker et al. |
| 7,727,192 | B2 | 6/2010 | Tokumoto et al. |
| 2004/0133111 | A1* | 7/2004 | Szczech et al. .............. 600/461 |
| 2004/0133168 | A1* | 7/2004 | Salcudean .............. A61B 10/04 604/164.13 |
| 2005/0154303 | A1* | 7/2005 | Walker ................ G01S 15/8979 600/443 |
| 2005/0181343 | A1 | 8/2005 | Ault et al. |
| 2007/0016035 | A1 | 1/2007 | Hashimoto |
| 2007/0032723 | A1* | 2/2007 | Glossop ........................ 600/424 |
| 2007/0112272 | A1 | 5/2007 | Park et al. |
| 2007/0129634 | A1 | 6/2007 | Hickey et al. |
| 2007/0167762 | A1 | 7/2007 | Kim et al. |
| 2007/0167808 | A1 | 7/2007 | Nozaki |
| 2008/0021322 | A1 | 1/2008 | Stone et al. |
| 2008/0221443 | A1* | 9/2008 | Ritchie et al. ................ 600/427 |
| 2008/0300491 | A1* | 12/2008 | Bonde et al. ................. 600/461 |
| 2009/0043205 | A1* | 2/2009 | Pelissier et al. .............. 600/446 |
| 2010/0022871 | A1 | 1/2010 | De Beni et al. |
| 2010/0196867 | A1 | 8/2010 | Geerligs et al. |
| 2010/0198068 | A1 | 8/2010 | Rivaz et al. |
| 2010/0268086 | A1 | 10/2010 | Walker et al. |

OTHER PUBLICATIONS

Neshat et al., "Real-Time Parametric Curved Needle Segmentation in 3D Ultrasound Images", 2nd IEEE RAS & EMBS International Conference on Biomedical Robotics and Biomechatronics, 2008, pp. 670-675.

Dong et al., "A Novel Method for Enhanced Needle Localization Using Ultrasound-Guidance", Proceedings of the 5th International Symposium on Advance in Visual Computing: Part I, 2009, 10 sheets.

Nolsoe et al., "EFSUMB—European Course Book: Interventional ultrasound", 2010, 38 sheets, http://www.efsumb.org/ecb/ecb-ch20-interventional-ultrasound.pdf.

Douglas et al., "Ultrasound-Guided Intervention: Expanding Horizons" Radiologic Clinics of North America, Jan. 31, 2011, pp. 415-428, vol. 39, Issue 3.

* cited by examiner

ULTRASOUND IMAGING APPARATUS

TECHNICAL FIELD

The following generally relates to imaging and finds particular application to ultrasound imaging, and more particularly to an apparatus that includes an ultrasound imaging portion and an instrument (e.g., a syringe, a scalpel, tweezers, a catheter, etc.) carrying portion that carries and employs an instrument installed therein based one or more images acquired by the ultrasound imaging portion.

BACKGROUND

A common site for a venipucture or intravenous (IV) insertion for obtaining a blood sample or intravenously administering a substance is the median cubital vein, which lies within the cubital fossa anterior to the elbow and is close to the surface of the skin. For a typical venipucture or IV insertion, the care giver (e.g., a phlebotomist, a nurse, a doctor, or other care giver) first visually locates this vein, and then prepares the skin area over the vein by cleaning the area (e.g., with alcohol) and prepares the vein by dilating the vein.

The care giver then proceeds to manually insert a needle, which is attached to a syringe, through the skin and into the vein at an angle in which the needle extends generally along the long axis of the vein. The care giver the draws back the plunger of the syringe to confirm whether the needle is in the vein or not based on whether blood is drawn into the syringe or not. A sufficient blood return generally indicates that the needle is indeed in the vein, and the care giver can draw blood or administer a substance via the vein. If unsuccessful, the care giver can either attempt to enter the same vein or identify a different vein to insert the needle into.

The literature has indicated that in the United States there are approximately one (1) billion venipunctures and more than two hundred (200) million peripheral intravenous (IV) insertions per year. For the venipunctures, the failure rate for the first attempt is approximately twenty percent (20%). For IV insertion, the success rate is nominally about eighty percent (80%), and only about thirty-three percent (33%) for difficult patients. In view of the foregoing, there is an unresolved need for other approaches for performing venipunctures and IV insertions.

SUMMARY

Aspects of the application address the above matters, and others.

In one aspect, an apparatus includes an ultrasound portion configured to acquire an image of a region of interest of a subject. The apparatus further includes an instrument carrying portion configured to carry and employ an instrument to perform a procedure at the region of interest based on the image. The ultrasound and instrument carrying portions are enclosed in the same enclosure. The apparatus, including both the ultrasound portion and instrument carrying portion, is configured to be transported and operated via at least a single hand of a user of the apparatus.

In another aspect, a method inserting an instrument, via an apparatus, in a region of interest of a subject identified via an image acquired by an ultrasound portion of the apparatus, wherein the apparatus encloses both the ultrasound portion and an instrument carrying portion that carries the instrument and that controls insertion of the instrument into the region of interest.

In another aspect, an ultrasound device includes an ultrasound portion with a two-dimensional transducer array configured to acquire at least two-dimensional planes of a region of a vessel of interest of a subject, a transducer controller that controls the transducer array to transmit and receive signals, an image processor that processes data acquired by the transducer array, and a display that visually presents the processed data. The ultrasound device further includes an instrument carrying portion with an instrument carrier configured to carry and employ a syringe loaded therein and an instrument carrier controller that controls the instrument carrier to position the syringe in the apparatus and insert a hypodermic needle of the syringe into a vein of a subject, employ the syringe, and withdraw the syringe to withdraw the hypodermic needle from the subject. A main controller of the device controls the transducer controller and the instrument carrier controller. The ultrasound and second portions are contained in a same enclosure and the ultrasound device is a hand-held, portable device, that is operated by a user via a single hand of the user.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIGS. 6A, 6B and 7C show a cross sectional side view of another non-limiting example of an instrument carrier loaded with a syringe instrument;

DETAILED DESCRIPTION

The following relates to an apparatus that includes an ultrasound portion and an instrument carrying portion configured to carry and/or employ, under operator control and/or automatically, an instrument which can be used in connection with procedure performed on a subject. By way of non-limiting example, in one instance the instrument carrying portion can be configured to carry a syringe with a hypodermic needle connected thereto and the ultrasound portion can be used to locate a vein of a subject in which to inject a substance into or draw blood from. The instrument carrying portion can then be used to facilitate inserting the hypodermic needle into the vein and administering the substance or drawing the blood via the syringe.

Although the following is mainly discussed in connection with the above syringe example, other suitable instruments include, but are not limited to, tubing (e.g., a catheter), a scalpel, tweezers, etc., which can be inserted and used in the vein, other vessel, and/or other area within the subject. In one non-limiting instance, the apparatus is an ultrasound device or unit that includes both the ultrasound portion and the instrument carrying portion. In one non-limiting embodiment, the apparatus is configured as a hand-held, portable device, with the ultrasound portion and the instrument carrying portion in the same enclosure, which can be carried and/or utilized by a user via a single or both hands of the user.

The capability to use only one hand to insert a needle and perform the procedure might allow the care giver flexibility with challenging or other patients. Moreover, with respect to the above-noted syringe example, the skill level of the operator need not be at the level commensurate with the skill level for an operator manually inserting the needle into the vessel, manually administering a substance or drawing blood, and manually withdrawing the needle, thereby simplifying the procedure and enabling a lower cost labor component to provide the procedure. Furthermore, the success rate of first insertion attempts may improve relative to attempting to insert the needle without using the apparatus.

Figure 1:
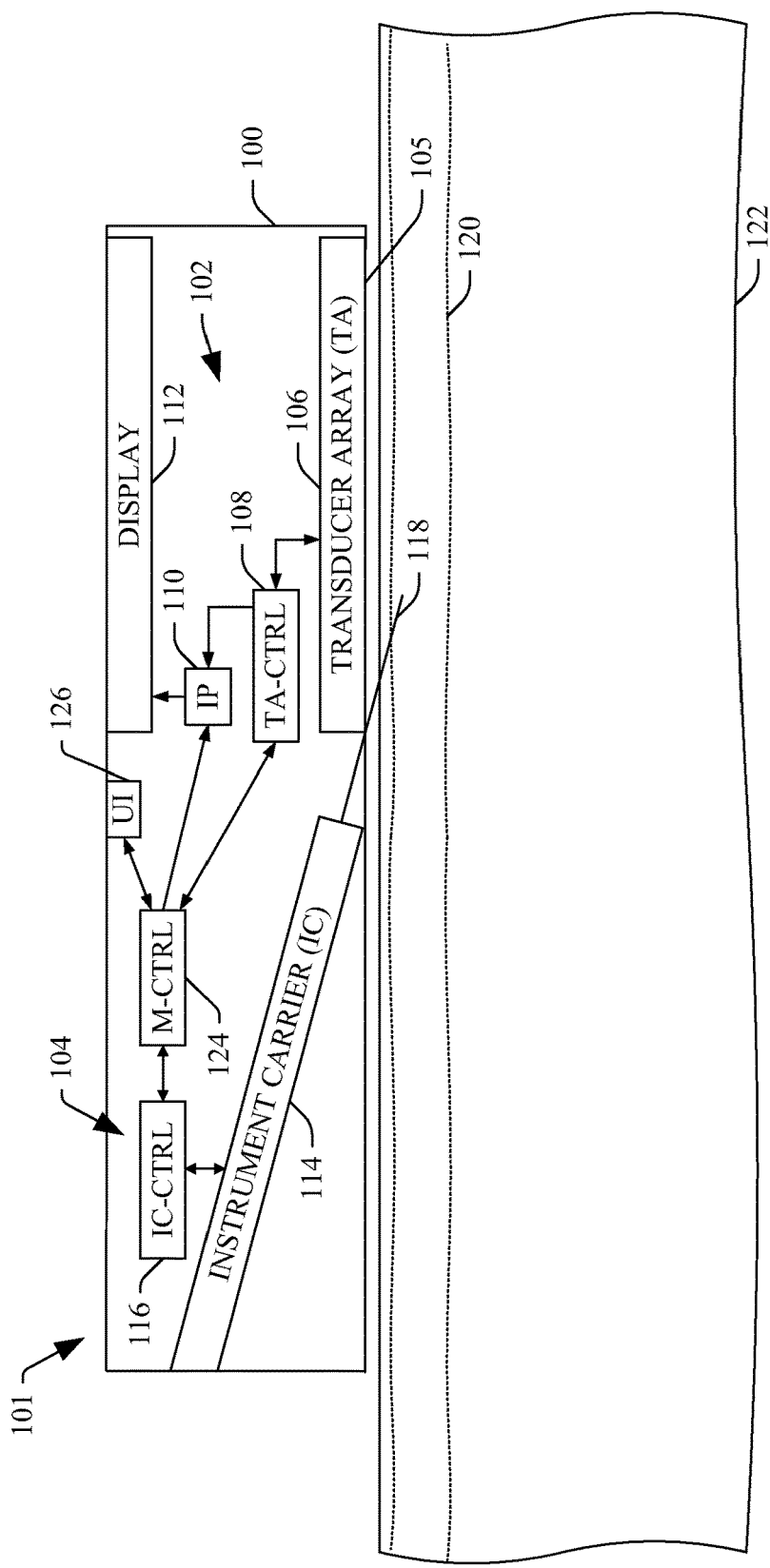
FIG. 1 schematically illustrates a hand-held, portable apparatus including both an ultrasound portion and an instrument carrying portion enclosed in the same enclosure.

Initially referring to FIG. 1, an apparatus 100 includes a single enclosure 101 housing an ultrasound portion 102 and an instrument carrying portion 104 configured to carry and employ an instrument. For sake of brevity and clarity, the following will be described in connection with an instrument such as a syringe (not visible), with a hypodermic needle 118 attached thereto, loaded in the apparatus 100 and configured to carry a substance, such as a fluid medicine or other fluid, and administer substance fluid to a subject 122 via a vessel 120 such as a vein of the subject 122 through the hypodermic needle 118.

The ultrasound portion 102 includes at least a transducer array (TA) 106, a transducer array controller (TA-CTRL) 108, an image processor (IP) 110 and a display 112. The transducer array 106 can include a one-dimensional and/or a two-dimensional array of transducer elements arranged in a linear, curved, circular, or other manner. The illustrated transducer array 106 includes a two-dimensional (2D) array of transducer elements. For example, the transducer array 106 may include an eight by eight, a thirty-two by thirty-two, a sixty-four by sixty-four, or other pixel array. The illustrated transducer array 106 can be used to acquire data for A-mode, B-mode, C-mode, etc. acquisitions, individually and in combination with color flow, Doppler flow, elastography, contrast harmonic, and/or other information.

The transducer array controller 108 includes transmit and receive circuitry and a switch that switches between transmit and receive circuitry. Generally, the transmit circuitry controls actuation of the transducer elements, which allows for steering and/or focusing the transmitted beam from predetermined origins along the array and at predetermined angles, and the receive circuitry's various processes receive echoes and generates and outputs a processed signal. In one non-limiting instance, the receive circuitry delays and sums received echoes, generating a focused signal for a single line through a scanned region of interest. Other suitable processing includes, but is not limited to, spatial compounding, filtering (e.g., FIR, IIR, etc.), and/or other processing.

The image processor (IP) 110 includes one or more processors that convert the signal from the transducer controller to generate data for display, for example, by converting the data to the coordinate system of the display. The display 112 can be used to present the converted data. By way of non-limiting example, in C-mode, the display can presents a plane of the vessel 120 that is parallel to a bottom or transducing surface 105 of the transducer array 106 and that shows the interior of the vessel 130 along the long axis of the vessel 120, including a portion of the needle 118 within the displayed interior of the vessel 120, when the needle 118 is inserted into the vessel 120, as is shown in FIG. 1. In the illustrated embodiment, the display 112 is part of the apparatus 100. In another embodiment, the display 112 is separate from the apparatus 100. In such an embodiment, the apparatus 100 includes a communications port through which the converted data can be transferred via a suitable medium (e.g., a cable, wirelessly, etc.) to the display 112.

The instrument carrying portion 104 includes an instrument carrier 114 configured to carry an instrument loaded or installed in the apparatus 100 and employ the instrument. In the illustrated embodiment, the instrument carrier 114 is fixed in place in the apparatus 100 and positioned at predetermined angle with respect to the surface 105 so the needle 118, before insertion, is at a suitable angle with respect to the surface 105 and hence the vessel 120. As described in connection with other embodiment herein, the instrument carrier 114 may alternatively be positional within the apparatus 100, allowing for selecting an angle for the instrument carrier 114 for a procedure from one or more suitable angles. Employment of the instrument and/or positioning of the instrument can be achieved via one or more motors, one or more belts, one or more gears, one or more lead or ball screws, one or more pistons, etc.

In the illustrated embodiment, the instrument carrier 114 is positioned in the apparatus 100 with respect to the transducer array 106 such that the needle 118 enters the imaging field of the transducer array 106 as the needle 118 advances beyond the bottom surface 105 and into the subject 122. In this illustrated embodiment, the needle 118 is imaged and displayed via the display 112 before the needle 118 breaks the skin of the subject 122. The needle 118 continues to be imaged and displayed via the display 112, with respect to the vein 120, as it is advanced into the vein 120. The needle 118 can also be imaged and displayed via the display 112, with respect to the vein 120, as it is withdrawn and retracted from the vein 120 and the skin.

The end of the instrument carrier 114, which is opposite of that which the needle 118 advances from, can be used to load and unload the instrument from the instrument carrier 114. In the illustrated embodiment, this end is at a back side of the apparatus 100. In other embodiments, this end can be located on a different side, the top, or the bottom of the apparatus 100. In one instance, the instrument carrier 114 is removable from the apparatus 100, and the instrument is manually loaded and unloaded from the instrument carrier 114 when the instrument carrier 114 is removed from the apparatus 100. In another instance, the instrument is pre-loaded in a removable disposable cartridge. The illustrated embodiment only shows a single instrument carrier 114, whereas the apparatus 100 may include one or more instrument carriers 114, which can be concurrently and/or sequentially utilized.

The instrument holding portion 104 further includes an instrument carrier controller (IC-CTRL) 116 configured to control the instrument carrier 114. As described in greater detail below, in one instance, the instrument carrier 114 includes a moveable (e.g., translatable, rotatable, and/or pivotal) region and one or more actuators, and the carrier controller 116 controls the one or more actuators to position the moving instrument holding portion and hence the instrument carried thereby and to employ the instrument for performing a procedure with the instrument. With further reference to the syringe example, this may include moving the moveable region to move the syringe towards the subject to advance the hypodermic needle 118 into the vein 120, advancing the plunger of the syringe relative to the barrel of the syringe to administer the substance (or retracting the plunger to draw blood), and moving the moveable region to move the syringe away from the subject and withdraw the hypodermic needle 118 from the vein 120.

A main controller (M-CTRL) 124 controls the transducer controller 108 and the instrument carrier controller 116. As described in greater detail below, the main controller 124 may control the instrument carrier controller 116 based on the ultrasound data from the transducer controller 108 and/or user input. Such control may include automatically controlling the instrument carrier controller 116 or controlling the instrument carrier controller 116 under operator input and/or interaction. Briefly, as an example, the main controller 124 may facilitate locating the vein 120 based on the acquired ultrasound data, notifying the user of the located vein, determining a suitable position (e.g., angle) of the instrument carrier 114 (for configurations in which the instrument carrier is moveable) based on information about the vein (e.g., depth, diameter, etc.) from the acquired data, requesting user authorization to automatically perform the procedure, wait for further instruction by the operator, etc.

A user interface 126 includes various input devices for interacting with the main controller 124 such as buttons, knobs, a keypad, a touch screen, etc. and/or visual and/or audible input and/or output devices. Such input devices can be variously located (e.g., on the front and/or one or more sides) on the apparatus 100 for easy access thereto, for example, when employing the apparatus using a single or two hands. A user can employ the user interface to identify a mode of operation such as A-mode, B-mode, C-mode, etc. The output devices can be used to present various information to the user such as information related to a located vein, the information about the vein (depth, diameter, etc.) a request for authorization to perform a procedure, a warning that the needle 118 is nearing or punctured a wall of the vein, the needle 118 exits the imaging field, or otherwise may need the attention of the user, etc.

The controllers 108, 116, and 124 may include one or more processor that execute computer readable instructions encoded or embedded on computer readable storage medium such as physical memory. Additionally or alternatively, at least one such instruction can be carried by a signal or carrier wave. Furthermore, one or more of the controllers 108, 116, and 124 may be located external to the apparatus 100. Moreover, although in FIG. 1 the apparatus 100 includes the single enclosure 101 which houses both the ultrasound and the instrument carrying portions 102 and 104, embodiments in which the ultrasound and the instrument carrying portions 102 and 104 are in different enclosures are contemplated herein.

Figure 2:
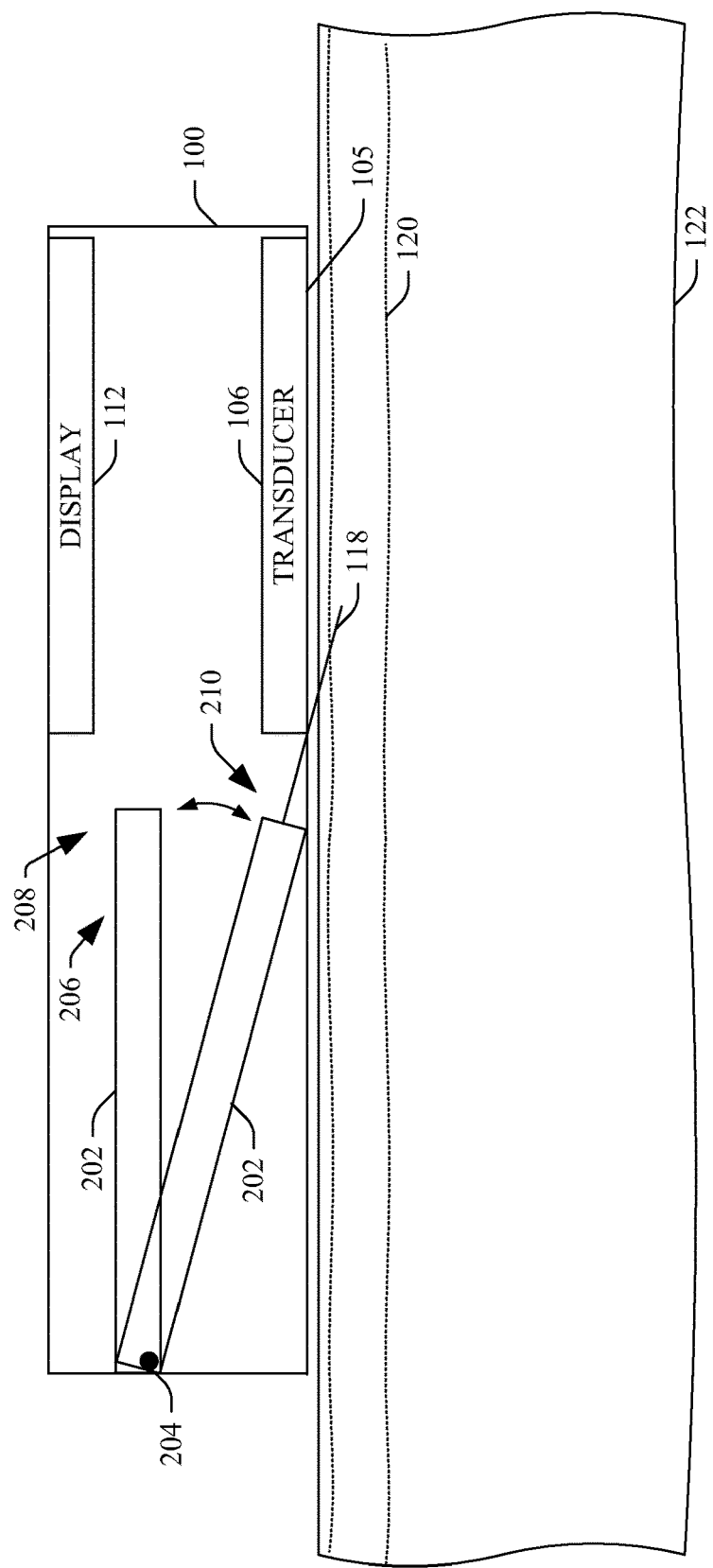
FIG. 2 schematically illustrates an embodiment of an instrument carrier, of the instrument carrying portion, configured to pivot between at least two positions.

FIG. 2 shows an embodiment in which the apparatus 100 includes a instrument carrier 202, which is substantially similar to the instrument carrier 114 of FIG. 1 except that the instrument carrier 202 is configured to pivot about a pivot 204 so that an end region 206 of the instrument carrier 202 from which the needle 118 protrudes can pivot between at least first and second positions 208 and 210. The instrument carrier controller 116 controls the pivoting of the instrument carrier 202.

In the illustrated embodiment, at the first position 208, the instrument carrier 202 is generally parallel to the surface 105. In other embodiments, the instrument carrier 202 can be angled with respect to the surface 105 at the first position 208. In the illustrated embodiment, at the second position 210, the instrument carrier 202 is at about the same angle, with respect to the surface 105, as the instrument carrier 114 of FIG. 1. In another embodiment, the angle can be different then the angle in FIG. 1.

In one instance, the first position 208 represents load and unload positions at which the instrument is loaded in and unloaded from the instrument carrier 202. The instrument carrier 202 may remain at the position 208 until the apparatus 100 is used in connection with a subject, for example, to locate a vein and/or administer a substance or draw blood, or the instrument carrier 202 may be pivoted before then, for example, after loading, regardless of when the apparatus is next used, to the position 210 or other position between 208 and 210.

In another embodiment, the instrument carrier 202, in the loading position, is adjacent to the bottom surface 105. In this embodiment, the pivot 204 is located at the end 206 at which the needle 118 extends from, and the instrument carrier 202 pivots at this end, moving the opposing (loading and unloading) end of the instrument carrier 202 (which is the end with the pivot 204 in FIG. 2) between at least two positions.

Note that in the illustrated embodiment, the loaded syringe instrument is retracted in the instrument carrier 202 at the position 208 such that the needle 118 is also within the instrument carrier 202 and not visible. In another embodiment, the needle 118 is partially or fully extended out of the instrument carrier 202 when the instrument carrier 202 is at the first position 208. Also note that the components 108, 110, 116, 124 and 126 are not shown in FIG. 2 in order to clearly show the instrument carrier 202.

Figure 3:
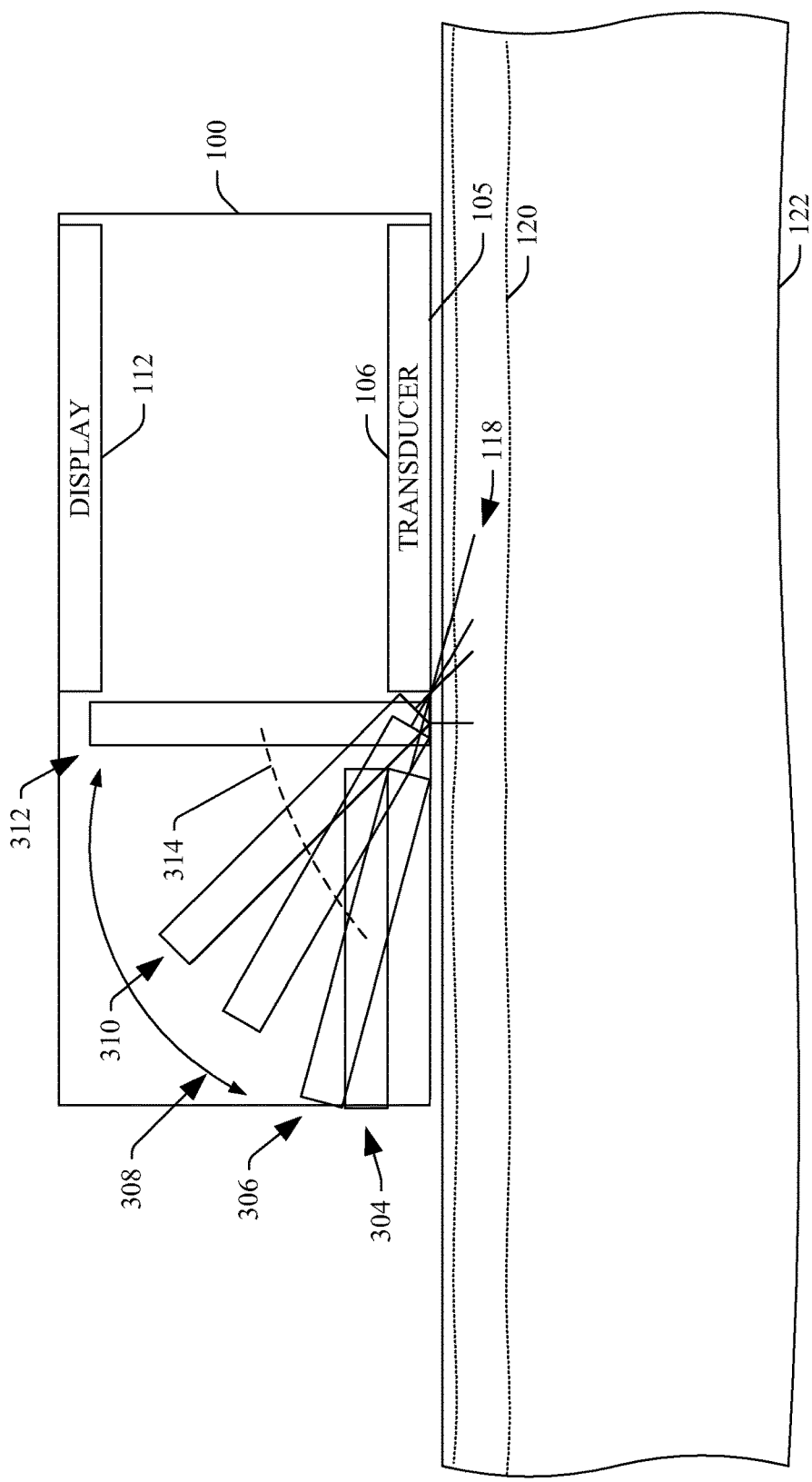
FIG. 3 schematically illustrates an embodiment of an instrument carrier, of the instrument carrying portion, configured to rotate and/or translate between at least two positions.

FIG. 3 shows an embodiment in which the apparatus 100 includes a instrument carrier 302, which is substantially similar to the instrument carrier 114 of FIG. 1 except that the instrument carrier 302 is configured to rotate and/or translate (x, y and/or z) to move between at least two positions, such as positions 304, 306, 308, 310, and 312, as shown in FIG. 3. In other embodiments, the instrument carrier 302 is configured to rotate and/or translate between more or less positions. Further, the movement may occur concurrently (translate and rotate), sequentially (translate then rotates, or vice versa) or a combination thereof.

In the illustrated embodiment, at the first position 304, the instrument carrier 302 is generally parallel to the surface 105 of the apparatus 100. In other embodiments, the instrument carrier 302 is angled with respect to the surface 105 at the first position 304. In one instance, the first position 304 represents load and unload positions at which an instrument such as example syringe instrument is loaded in and unloaded from the apparatus 100. Similar to FIG. 2, the instrument carrier 302 may remain in the position 304 until the apparatus 100 is used in connection with a subject or may be moved before then to another position.

The positions 306 to 312 represent different procedure positions, from close to being parallel to the surface 105 to be perpendicular to the surface 105. In the illustrated embodiment, at the position 312, the needle 118 does not enter the imaging field during the procedure. At the positions 306 to 310, the needle 118 enters the imaging field during the procedure, and, as such, the needle 118 can be observed during insertion into the vein 120 and retraction out of the vein 120. Note also that in the illustrated embodiment, the syringe is advanced different distances in the instrument carrier 306 as shown by the different lengths of the protruding needle 118.

In the illustrated embodiment, the instrument carrier controller 116 controls the movement of the instrument carrier 302 along a path 314. In one instance, the particular position is selected before identifying the vein. In another instance, the vein is first located and then a suitable position is identified based on an orientation (e.g., the depth, angle, etc.) and/or a physical characteristic (e.g., diameter, segment length, etc.) of the vein, a length of the needle 118, and/or other information. This may facilitate ensuring that the needle 118 does not go through one side out another side of the vein 120. Similar to FIG. 2, the components 108, 110, 116, 124 and 126 are not shown in FIG. 3 in order to clearly show the instrument carrier 202.

Figure 4:
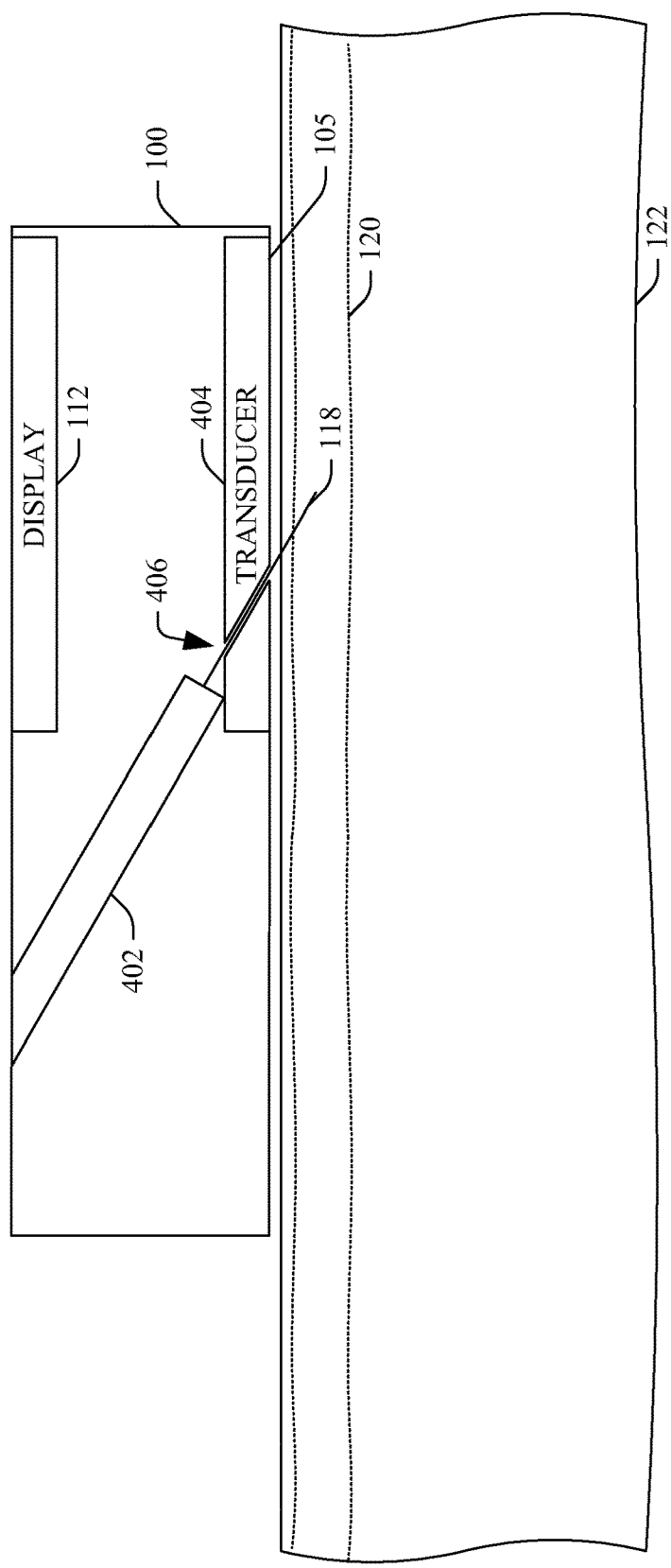
FIG. 4 schematically illustrates an embodiment in which the transducer array includes an opening through which an instrument carried by the instrument carrier extends from within the apparatus to outside of the apparatus for a procedure.

In FIG. 4, the apparatus 100 includes an instrument carrier 402 and a transducer array 402 that has a material free region 406 through which the needle 118 extends from the instrument carrier 402 inside of the apparatus 100 to the surface 105 and out of the apparatus 100 for performing a procedure on the subject. In the illustrated embodiment, the material free region 406 is a port or entry way that is shaped to be slightly larger than the needle diameter. In other embodiments, the material free region 406 may be a slit that extends across the entire transducer 404 or other shape.

In yet another embodiment, such as where there are more than one instrument carrier 402 and/or the instrument carrier 402 is moveable (e.g., as shown FIGS. 2 and 3), the transducer array 404 may include multiple material free regions 406 for different instrument carrier 402 and/or corresponding to different instrument carrier special orientations. Moreover, a single instrument carrier 402 may utilize multiple material free regions 406, for example, where a first attempt to insert the needle 118 into the vein 120 using a first material free region 406 is not successful and a subsequent attempt is made using a different material free region 406.

In the illustrated embodiment, unlike FIGS. 1-3, the instrument carrier 402 is at angle with respect to the surface 105 and accessible from a top of the apparatus to load and unload the syringe from the instrument carrier 402. Similar to FIG. 2, the components 108, 110, 116, 124 and 126 are not shown in FIG. 4 in order to clearly show the instrument carrier 202.

FIGS. 5A, 5B and 5C show a cross sectional side view of an example instrument carrier 114 (or 202, 302 and/or 402) with a syringe 502 loaded or installed therein. The syringe 502 includes a cylindrical barrel 504 configured to hold a fluid such as a liquid medicine, and a plunger 506 configured to slide through the barrel 504 under pressure and push the fluid out of an end of the barrel 504 connected to the needle 118 and through the needle 118.

In the illustrated embodiment, the example instrument carrier 114 includes a first drive system including a motor 508, a ball screw 510 (driven by the motor 508), and a ball nut 512 moveably affixed to the ball screw 510 and coupled to the barrel 504. A second drive system includes a motor 514 affixed to the ball nut 512, a ball screw 516 (driven by the motor 514), and a ball nut 518 moveably affixed to the ball screw 516 and coupled to the plunger 506.

As shown in FIG. 5B, the instrument carrier controller 116 first drives the motor 508 to turn the ball screw 510 which draws the ball nut 512 and hence the syringe 502 towards the subject. As shown in FIG. 5C, the instrument carrier controller 116 then drives the motor 514 to turn the ball screw 516 which draws the ball nut 514 and hence the plunger 506 towards the end of the syringe 502 affixed to the needle 118. The motors 508 and 514 are also used to retract the syringe 502.

An optional spring 520 is disposed between the syringe 502 and the end of the instrument carrier 114 through which the needle 118 extends. As shown in FIG. 5A, the spring 520 may help hold the syringe 502 in the instrument carrier 202, for example, in a position in which the needle 118 is inside the apparatus 100. As shown in FIGS. 5B and 5C, the spring 520 is in a compressed state, which may facilitate holding the syringe 502 in place for the procedure as well as facilitate unloading the syringe 502 by urging the syringe 502 towards the unloading end of the instrument carrier 114.

FIGS. 6A, 6B and 6C show a cross sectional side view of another example instrument carrier 114 (or 202, 302 and/or 402) with the syringe 502 loaded or installed therein like in FIGS. 5A, 5B and 5C.

In the illustrated embodiment, the example instrument carrier 114 includes a first drive system including a first set of motor driven wheels 602, which physically contact the barrel 504. A second drive system includes a second set of motor driven wheels 604, which initially physically contacts the barrel 504 (FIG. 6A) and then physically contacts the plunger 506 (FIGS. 6A and 6B).

As shown in FIG. 6A, the instrument carrier controller 116 first drives the first and second sets of wheels 602 and 604 to move the syringe 502 towards the subject. As shown in FIGS. 6B and 6C, the instrument carrier controller 116 then drives the second set of wheels 604 to move the plunger 506 towards the end of the syringe 502 affixed to the needle 118. The wheels 602 and 604 can also be used to retract the syringe 502.

A pre-loaded spring 606 is disposed between the syringe 502 and the end of the instrument carrier 114 through which the needle 118 extends. As shown in FIG. 6A, the spring 606 is in its compressed states and carries the end of the syringe 502. As shown in FIGS. 6B and 6C, the spring 606 is stretched and in a tension state, which may facilitate unloading the syringe 502 by pulling the syringe 502 towards the unloading end of the instrument carrier 114.

It is to be appreciated that FIGS. 5A, 5B and 5C and FIGS. 6A, 6B and 6C are shown for explanatory purposes and are not limiting. Essentially any mechanism that can be used to move the barrel 504 and the plunger 506 can be utilized with the apparatus 100. Examples of suitable motors include AC and/or DC motors, and the drive system may include a belt (e.g., smooth or cogged), one or more gears, a bearing, a slide, a piston, a lead screw, a balls screw (FIG. 5), at least one wheel (FIG. 6), etc.

Moreover, a position sensing device such as an encoder or the like may be used to track the location of the barrel 504, the plunger 506, and/or the needle 118, and can be for closed loop servo control. Furthermore, for blood draws, the plunger 508 is initially in the barrel 504 and retracted from the barrel 504 instead of being advanced into the barrel 506.

Figure 7:
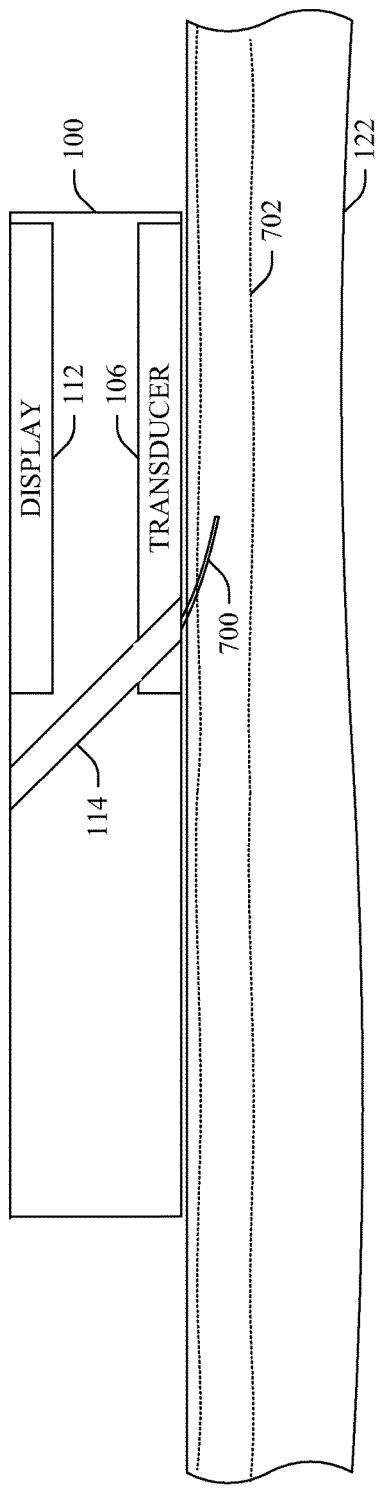
FIG. 7 schematically illustrates an embodiment of an instrument carrier configured to carry and move a catheter instrument in connection with a procedure.

FIG. 7 illustrates an embodiment in which the instrument carrier 114 (202, 302 and/or 402) is utilized to advance a catheter 700 into a vessel 702. By way of non-limiting example, the instrument carrier 114 can be utilized to advance the catheter 700 from the femoral artery at the groin of a subject to the heart of the subject for a cardiac catheterization, stent insertion, plaque removal, and/or other procedure. As discussed herein, the ultrasound portion 104 can be used to locate such a vessel. In other embodiments, a catheter is advanced to another region such as the brain, the lungs, and/or other tissue of interest.

Figure 8:
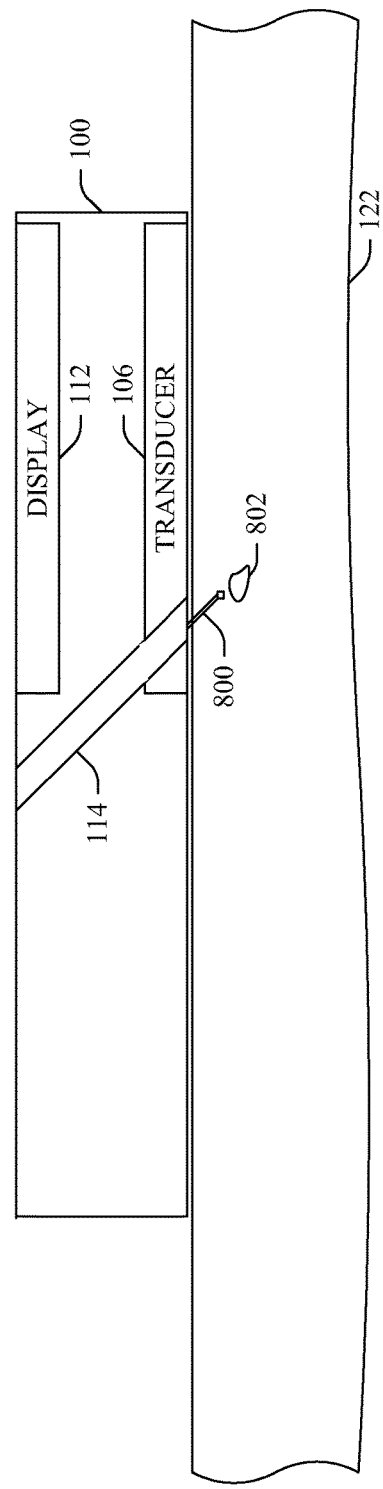
FIG. 8 schematically illustrates an embodiment of an instrument carrier configured to carry and move a tweezer instrument in connection with a procedure.

FIG. 8 illustrates an embodiment in which the instrument carrier 114 (202, 302 and/or 402) is utilized to maneuver an instrument such as tweezers 800 for removing foreign body matter 802 (e.g., metal, glass, a growth, etc.) under the skin of the subject 122. Note the size and location of the illustrated matter 802 is for explanatory purposes. Other suitable instrumentation may include a scalpel, a biopsy needle, and/or other instrumentation.

Figure 5:
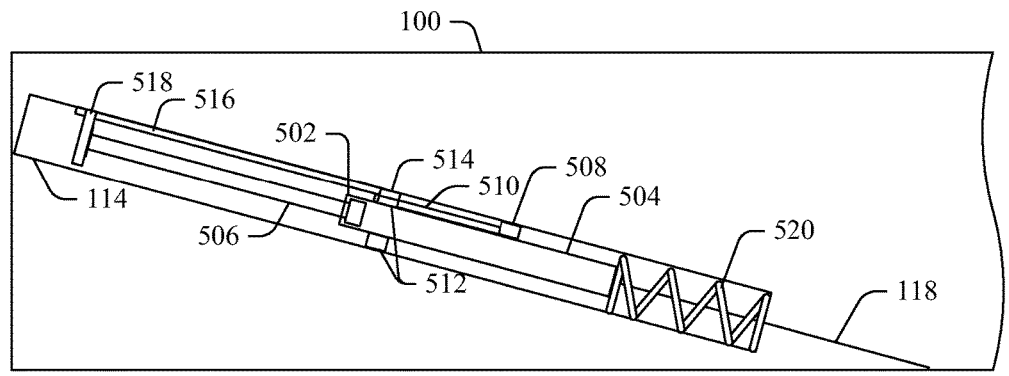
FIGS. 5A, 5B and 5C show a cross sectional side view of a non-limiting example of an instrument carrier loaded with a syringe instrument.
Figure 5:
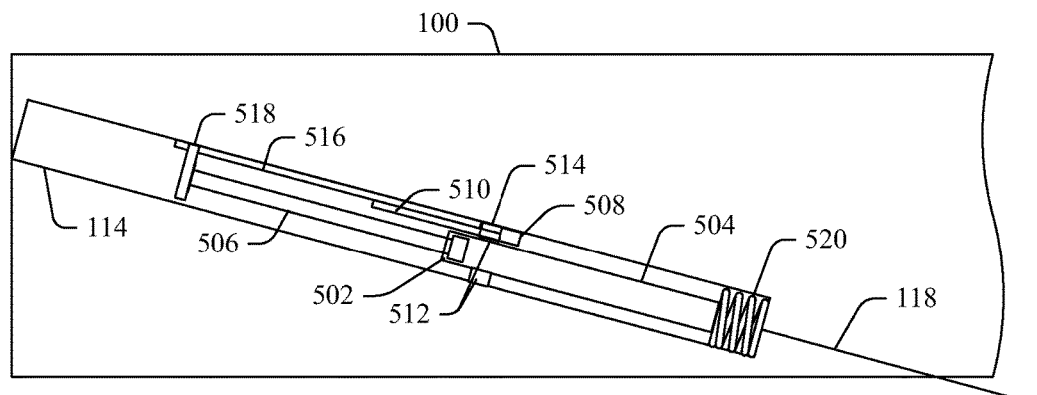
Figure 5:
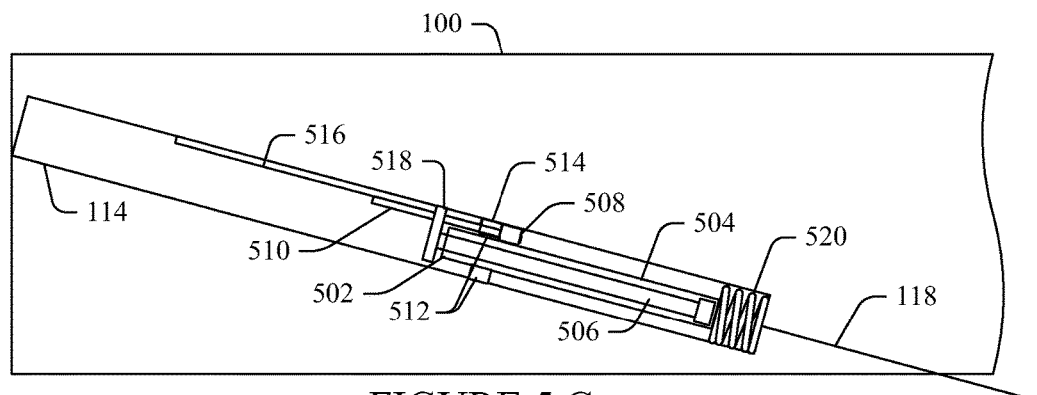
Figure 6:
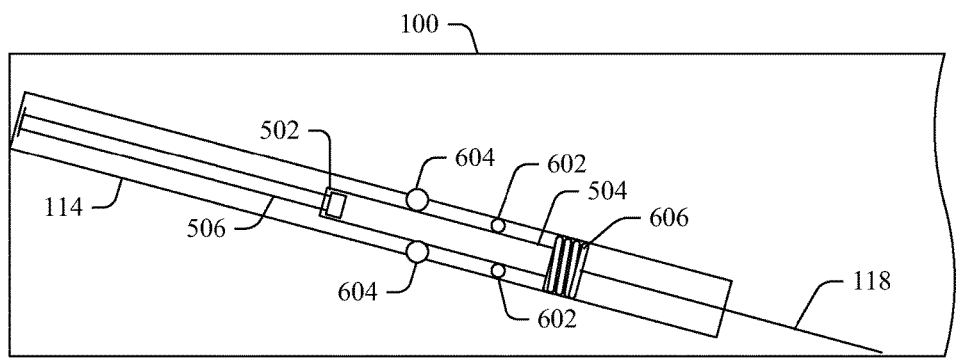
Figure 6:
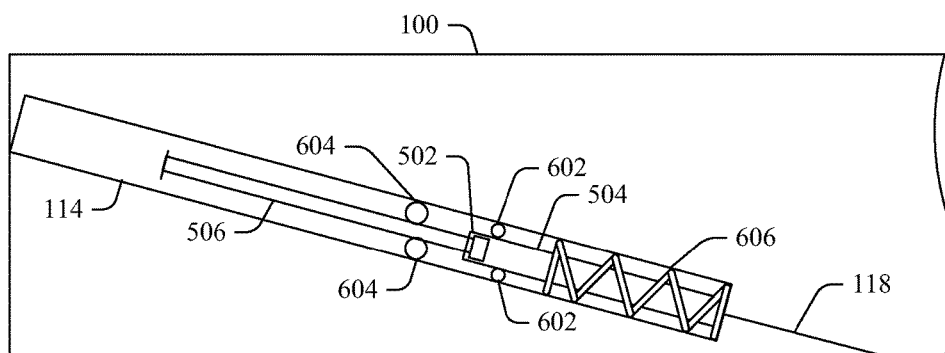
Figure 6:
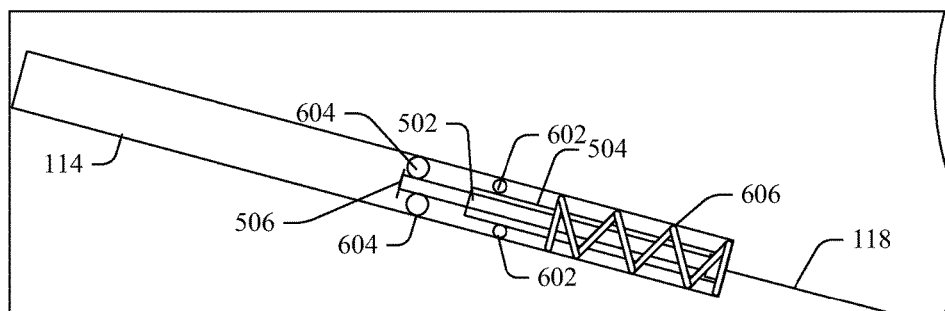

With FIGS. 7 and 8, drives mechanisms similar to those discussed in connection with FIGS. 5 and/or 6, other drive mechanism, and/or a combination thereof may be to advance and retract the catheter 700, the tweezers 800, the scalpel, the biopsy needle, etc. By way of example, the wheels 602 and 604 discussed in connection with FIG. 6 can be used to advance and retract the catheter tubing of FIG. 7.

Figure 9:
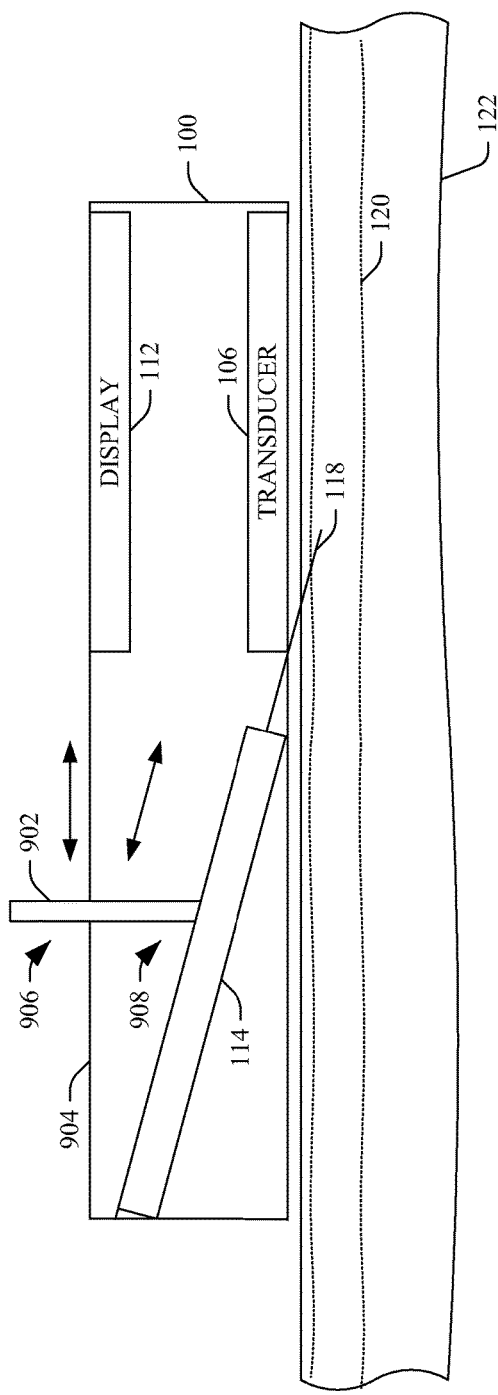
FIG. 9 schematically illustrates an embodiment of an instrument carrier in which the instrument therein is moved manually by a user via a single lever.

FIG. 9 illustrates an embodiment in which the instrument carrier 114 configured to be manually controlled via a single control. In this embodiment, a lever 902 is configured to slide back and forth with respect to a top surface 904 of the apparatus 100. The lever 902 includes a first end 906 that extends out of the top surface 904 and a second end 908 coupled to the moving portion of the instrument carrier 114. In operation, a user slides pushes or pulls the first end 906 either forwards or backwards which causes the second end 908 to advance and retract a syringe installed in the instrument carrier in order to inject and withdraw the needle 118. In the illustrated embodiment, a single lever 902 is utilized move both the syringe barrel and the syringe plunger.

Figure 10:
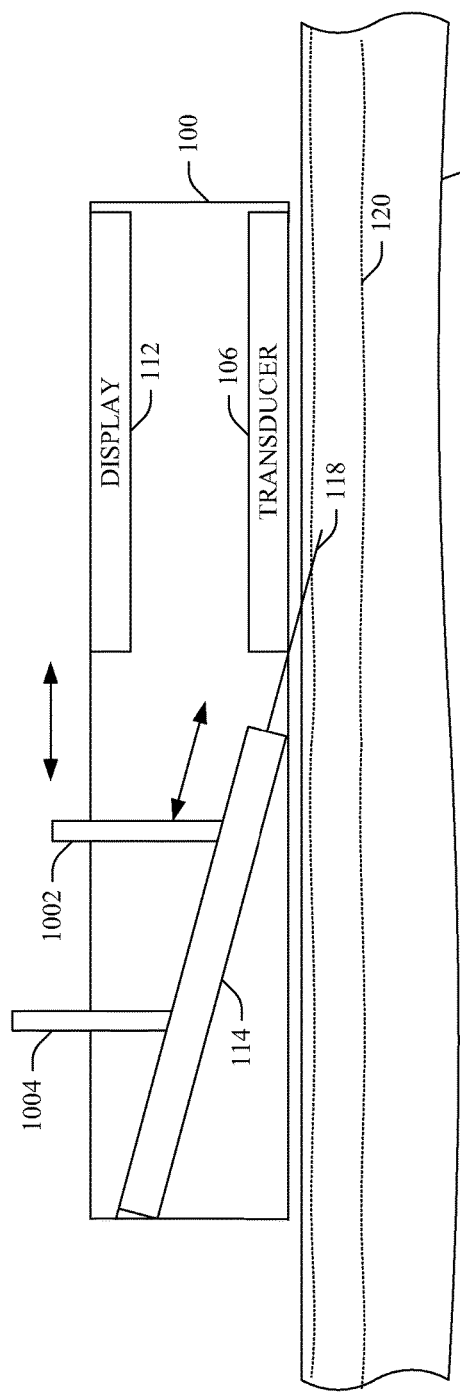
FIG. 10 schematically illustrates an embodiment of an instrument carrier in which the instrument therein is moved manually by a user via multiple levers.

FIG. 10 illustrates an embodiment in which the instrument carrier 114 configured to be manually controlled via multiple controls. In this embodiment, levers 1002 and 1004 are configured substantially similar to the lever 902 of FIG. 9 except that the lever 1002 controls movement of the entire syringe via the barrel and the lever 104 controls movement only of the plunger.

Figure 11:
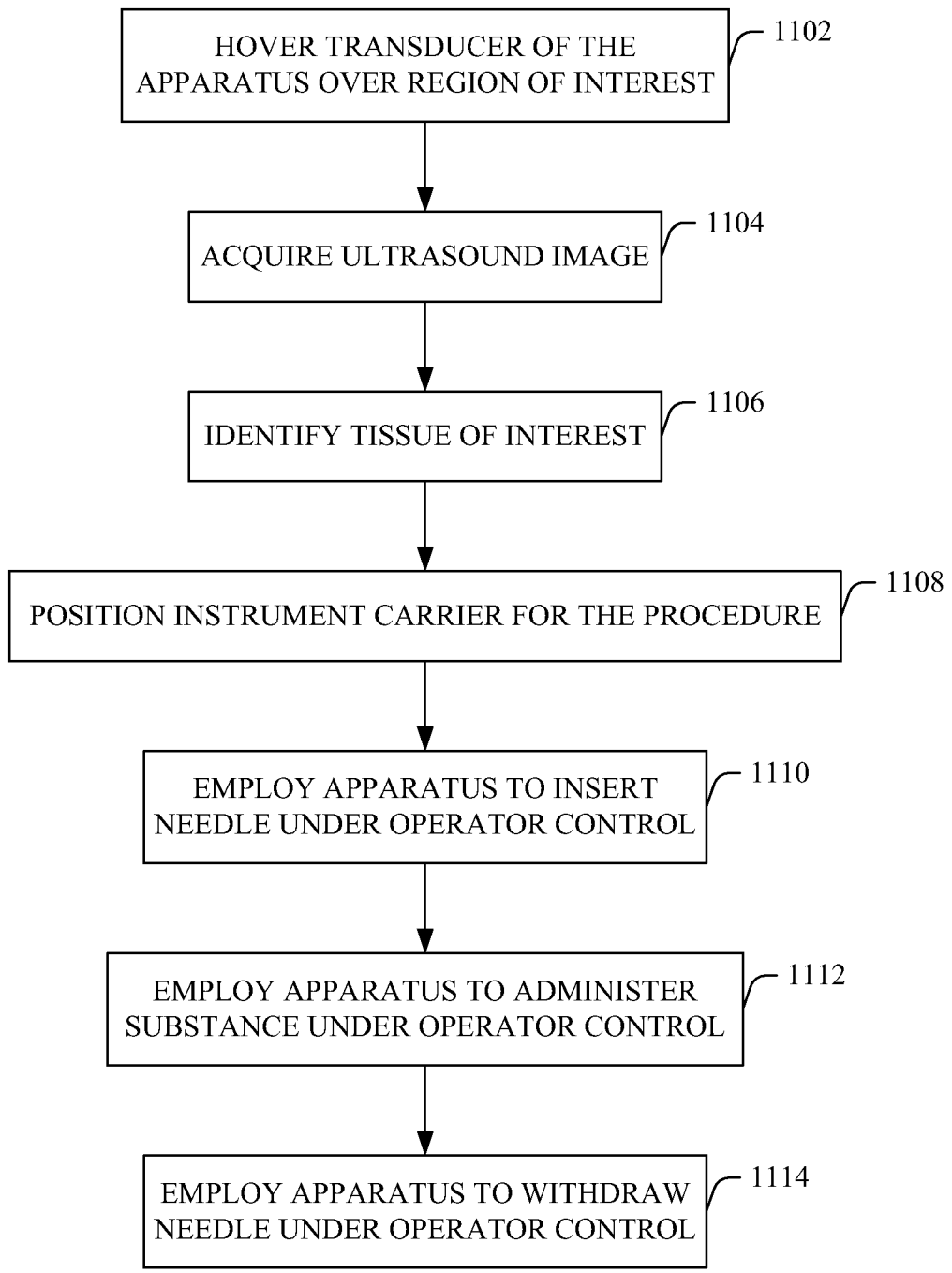
FIG. 11 illustrates an example method for using the apparatus to perform a procedure under operator control.

FIG. 11 illustrates a method for using the apparatus 100 described herein.

Similar to above, the method is discussed in connection with a syringe instrument for explanatory purposes, and other instruments such as tubing, scalpels, tweezers, etc. are contemplated.

At 1102, a user hovers the transducer array of the apparatus 100 over a region of the subject including tissue of interest such as a vessel of interest like the vessel 120.

At 1104, the ultrasounds portion 102 of the apparatus 100 acquires and displays data indicative of the region of interest. In one instance, the ultrasounds portion 102 is run in C-mode, and the data represents a plane of the vessel 120 at a predetermined depth in the subject.

At 1106, the tissue of interest is identified in the acquired data. The vessel 120 may be manually identified by the user through visual inspection of the displayed image and/or via the controller 108 and/or 124 of the apparatus 100 analyzing the acquired data. Where the vessel is identified via the controller 108 and/or 124, the apparatus 100 can notify the user via visual, audio, tactile and/or other feedback through the user interface 126 and/or otherwise. The user may confirm or reject the identification made by the apparatus 100.

At 1108, where the instrument carrier is configured to at least one of pivot, rotate, or translate (x, y and/or z), the instrument carrier is positioned (e.g., oriented within the apparatus 1110), manually or automatically, for a procedure based on information about the identified tissue of interest (e.g., depth, diameter, etc.). The position may also be determined based on information about the substance to be injected, the length of the needle, and/or other information. Where the instrument carrier is not configured to move, this act is omitted.

At 1110, the user employs the user interface to send a signal to the apparatus 100 indicating that the needle 118 should be inserted into the vessel 120, and, in response to the apparatus receiving such signal, the controller 116 advances the syringe 502 thereby inserting the needle 118 into the vessel 120.

At 1112, the user employs the user interface to send a signal indicating that the substance in the barrel 504 of the syringe 502 should be injected into the vessel 120 (or blood should be obtained from the vessel 120), and, in response to the apparatus receiving such signal, the controller 116 advances (or retracts) the plunger 506 thereby injecting the substance into (or withdrawing blood from) the vessel 120.

At 1114, the user employs the user interface to send a signal indicating that the needle 118 should be withdrawn from the vessel 120, and, in response to the apparatus receiving such signal, the controller 116 retracts the syringe 502 thereby withdrawing the needle 118 from the vessel 120.

In one instance, in acts 1110, 1112 and/or 1114, the user continuously provides the signal (e.g., press a button) for the needle to move the syringe 502 and/or barrel 506 to its destination in that termination of the signal (e.g., release of the button) results in ceasing movement.

In another instance, the signal causes the syringe 502 and/or barrel 506 to automatically move and a subsequent signal can be sent to stop the movement. Moreover, activation and/or deactivation may require a single action by the user (e.g., single button press) or multiple concurrent or sequential actions (e.g., multiple button press).

In another instance, the user does not have to provide the activation signal for all three acts 1110-1114.

Figure 12:
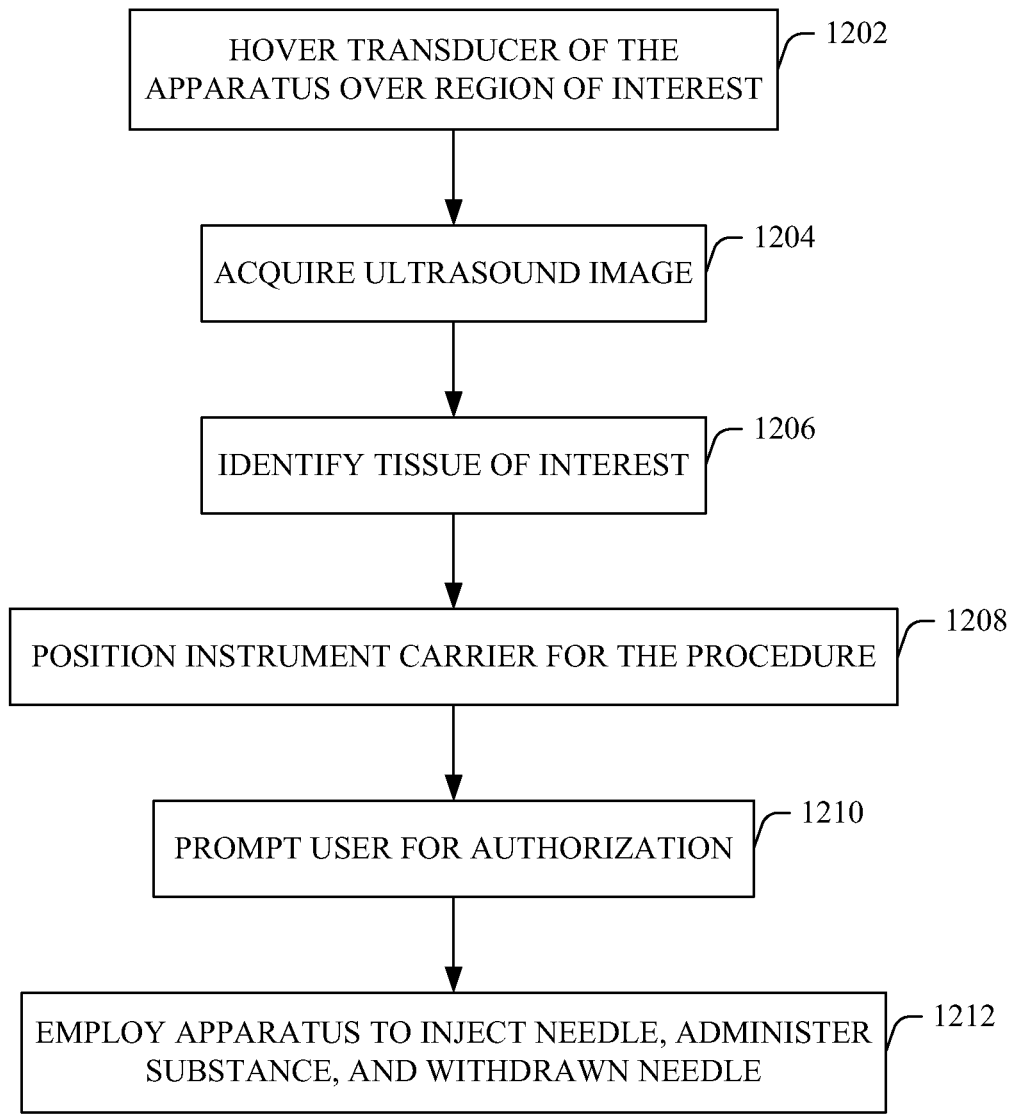
FIG. 12 illustrates an example method for using the apparatus to perform a procedure automatically under control of the apparatus.

FIG. 12 illustrates a method for using the apparatus 100 described herein.

Similar to above, the method is discussed in connection with a syringe instrument for explanatory purposes, and other instruments such as tubing, scalpels, tweezers, etc. are contemplated.

At 1202, a user hovers the apparatus 100 over a region of the subject including the vessel of interest.

At 1204, the ultrasounds portion 102 of the apparatus 100 acquires and displays data indicative of the region of interest. Like act of 1104, in one instance, the ultrasounds portion 102 is run in C-mode, and the data represents a plane at a predetermined depth in the subject that is parallel to the bottom of the transducer array 106.

At 1206, the vessel of interest is identified in the acquired data as described herein.

At 1208, where the instrument carrier 114 is configured to at least one of pivot, rotate, or translate (x, y and/or z), the apparatus positions the instrument carrier 114, manually or automatically, based on information (e.g., depth, diameter, etc.) about the identified vessel.

At 1210, the apparatus 100 prompts the user via the user interface 126 for authorization to automatically perform the procedure.

At 1212, in response to receiving a signal indicating suitable user authorization, the apparatus automatically controls the instrument carrier 114 to insert the needle, inject the substance (or withdrawn a blood sample), and withdraws the needle. Such authorization may include entering a password or the like.

Of course, the user can pause and/or stop the apparatus 100 at any time during act 1212. Furthermore, such authorization may be required before each or at least two of the insertion of the needle 118, the administration of the fluid in the barrel 506, and the withdrawing of the needle 118.

It is to be appreciated that the order of the method acts herein is provided for explanatory purposes and is not limiting. As such, one or more of the acts may occur in a different order. Furthermore, one or more of the acts may be omitted and/or one or more additional acts may be added.

It is to be appreciated that the methods herein may be implemented by one or more processors executing computer executable instructions stored, encoded, embodied, etc. on computer readable storage medium such as computer memory, non-transitory storage, etc. In another instance, the computer executable instructions are additionally or alternatively stored in transitory or signal medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A portable ultrasound apparatus, comprising:
   a single enclosure with at least two sides, including a first side and a second side disposed opposite the first side across a gap there between, the single enclosure housing:
   a transducer array with a transducing area, wherein the transducer array is disposed in the first side, and the first side includes the transducing area and a non-transducing area;
   an image processor disposed between the first and the second sides;
   a display with a display area, wherein the display is disposed in the second side, and the second side includes the display area and a nondisplay area, wherein the transducer array and the display are disposed opposite each other across the gap; and
   an instrument carrier disposed between the first and the second sides and configured to carry an instrument, wherein the instrument carrier includes an elongated hollow shaft with first and second ends,
   wherein at least one of the first and second ends is entirely closed and another of the first and second ends includes at least one opening at a central region of the corresponding end, and
   wherein the instrument carrier further comprises a first drive system physically contacts a barrel of a syringe installed in the instrument carrier and translates the barrel of the syringe installed in the instrument carrier.

2. The apparatus of claim 1, wherein the instrument is the syringe with the barrel, a hypodermic needle and a plunger that translates in the barrel, the display displays ultrasound data indicative of an interior of an object, and the first drive system translates the barrel and the hypodermic needle in the instrument carrier towards the object and the hypodermic needle into a region of interest of the object, wherein the region of interest, including a needle entry point into the region of interest, is visually represented in the displayed ultrasound data.

3. The apparatus of claim 2, further comprising:
   a user interface, wherein the first drive system automatically translates the barrel in response to the apparatus receiving, via the user interface, a signal indicative of a user authorization to insert the needle into the region of interest.

4. The apparatus of claim 2, further comprising: a second drive system that translates the plunger in the barrel towards the hypodermic needle.

5. The imaging transducer of claim 4, further comprising: an instrument carrier controller, wherein the second drive system includes a motor, a ball screw, and a ball nut, and the instrument carrier controller drives the motor, which turns the ball screw, which draws the ball nut that urges the plunger towards the region of interest.

6. The apparatus of claim 2, wherein the first drive system translates the barrel and thereby the hypodermic needle away from the vein, retracting the syringe, thereby withdrawing the hypodermic needle from the region of interest.

7. The apparatus of claim 6, further comprising:
   a user interface, wherein the first drive system automatically retracts the syringe in response to the apparatus receiving a signal, via the user interface.

8. The imaging transducer of claim 2, further comprising: an instrument carrier controller, wherein the first drive system includes a motor, a ball screw, and a ball nut, and the instrument carrier controller drives the motor, which turns the ball screw, which draws the ball nut that urges the barrel towards the region of interest.

9. The imaging transducer of claim 2, further comprising: a second drive, wherein the first drive system includes a first set of motor driven wheels which physically contact the barrel, and the second drive system includes a second set of motor driven wheels which alternatively physically contacts the barrel or the plunger.

10. The apparatus of claim 1, wherein the instrument carrier is disposed at a fixed position in the apparatus.

11. The apparatus of claim 1, wherein the instrument carrier pivots, via a pivot, within the enclosure between at least two positions in the apparatus.

12. The apparatus of claim 11, wherein the pivot is located at a first end of the instrument carrier which is opposite an end of the instrument carrier through which the instrument translates towards the region of interest.

13. The apparatus of claim 11, wherein pivoting the instrument carrier does not pivot the enclosure.

14. The apparatus of claim 1, wherein the display and the transducer array are spatially oriented parallel to each other.

15. The apparatus of claim 1, wherein the transducing area faces away from the second side.

16. The apparatus of claim 15, wherein the transducer array includes a non-material region extending completely through the transducer array and the transducing area.

17. The apparatus of claim 16, wherein the instrument carrier is disposed in part directly between the first and second sides.

18. The apparatus of claim 17, wherein the instrument carrier extends from the second side.

19. The apparatus of claim 15, wherein the display area faces away from the second side.

20. The apparatus of claim 1, wherein the single enclosure includes a third side of the at least two sides which is transverse to the first and second sides, and the instrument carrier extends from the third side.

21. The apparatus of claim 1, wherein at least one of the first or second sides includes a rigid material.

22. A portable ultrasound apparatus, comprising:
a single enclosure with at least two sides, including a first side and a second side disposed opposite the first side across a gap there between, the single enclosure housing:
   a transducer array with a transducing area, wherein the transducer array is disposed in the first side, and the first side includes the transducing area and a non-transducing area;
   an image processor disposed between the first and the second sides;
   a display with a display area, wherein the display is disposed in the second side, and the second side includes the display area and a nondisplay area, wherein the transducer array and the display are disposed opposite each other across the gap; and
   an instrument carrier disposed between the first and the second sides and configured to carry an instrument, wherein the instrument carrier includes an elongated hollow shaft with first and second ends,
   wherein at least one of the first and second ends is entirely closed and another of the first and second ends includes at least one opening at a central region of the first and second ends, and wherein the instrument carrier further comprises a first drive system that physically contacts a barrel of a syringe and pushes or pulls the barrel of the syringe.

23. A portable ultrasound apparatus, comprising:
a single enclosure with at least two sides, including a first side and a second side disposed opposite the first side across a gap there between, the single enclosure housing:
   a transducer array with a transducing area, wherein the transducer array is disposed in the first side, and the first side includes the transducing area and a non-transducing area;
   an image processor disposed between the first and the second sides;
   a display with a display area, wherein the display is disposed in the second side, and the second side includes the display area and a non-display area, wherein the transducer array and the display are disposed opposite each other across the gap; and
   an instrument carrier disposed between the first and the second sides and configured to carry an instrument, wherein the instrument carrier includes an elongated hollow shaft with first and second ends,
   wherein at least one of the first and second ends is entirely closed and another of the first and second ends includes at least one opening at a central region of the first and second ends, and
   wherein the instrument carrier further comprises a first drive system that physically contacts a barrel of a syringe and advances or retracts the barrel of the syringe and one or more actuators that translate the instrument carrier; and
an instrument carrier controller disposed between the first and second sides configured to control the one or more actuators.

* * * * *